United States Patent [19]

Hoffman et al.

[11] Patent Number: 5,314,489
[45] Date of Patent: May 24, 1994

[54] HIP PROSTHESIS

[75] Inventors: William H. Hoffman, Canton; Richard D. Scott, Dedham, both of Mass.; James A. Rand, Rochester, Minn.

[73] Assignee: Johnson & Johnson Orthopaedics, Inc., Raynham, Mass.

[21] Appl. No.: 973,198

[22] Filed: Nov. 6, 1992

Related U.S. Application Data

[63] Continuation of Ser. No. 769,030, Sep. 30, 1991.

[51] Int. Cl.$^5$ .......................... A61F 2/32; A61F 2/36; A61F 2/30
[52] U.S. Cl. ............................ 623/22; 623/18; 623/23
[58] Field of Search ................. 623/16, 18, 22, 23

[56] References Cited

U.S. PATENT DOCUMENTS

| | | | |
|---|---|---|---|
| D. 254,987 | 5/1980 | Treace et al. | D24/33 |
| D. 280,020 | 8/1985 | Homsy | D24/33 |
| 3,982,281 | 9/1976 | Giliberty | 623/23 |
| 4,068,324 | 1/1978 | Townley et al. | 3/1.913 |
| 4,314,381 | 2/1982 | Koeneman | 623/22 |
| 4,454,612 | 6/1984 | McDaniel et al. | 623/23 |
| 4,514,865 | 5/1985 | Harris | 3/1.913 |
| 4,516,277 | 5/1985 | Butel | 623/23 |
| 4,563,778 | 1/1986 | Roche et al. | 623/23 |
| 4,566,138 | 1/1986 | Lewis et al. | 623/22 |
| 4,642,124 | 2/1987 | Cooke | 623/23 |
| 4,678,472 | 7/1987 | Noiles | 623/22 |
| 4,783,192 | 11/1988 | Wroblewski et al. | 623/23 X |
| 4,795,472 | 1/1989 | Crowninshield et al. | 623/23 |
| 4,827,919 | 5/1989 | Barbarito et al. | 623/22 X |
| 4,840,632 | 6/1989 | Kampner | 623/22 |
| 4,851,004 | 7/1989 | Homsy | 623/16 |
| 4,871,369 | 10/1989 | Muller | 623/23 |
| 4,955,912 | 9/1990 | Berchem | 623/23 X |
| 5,116,380 | 5/1992 | Hewka et al. | 623/23 |

FOREIGN PATENT DOCUMENTS

| | | | |
|---|---|---|---|
| 0357546 | 3/1990 | European Pat. Off. | A61F 2/30 |
| 0359485 | 3/1990 | European Pat. Off. | A61F 2/36 |
| 0501116 | 9/1992 | European Pat. Off. | A61F 2/30 |
| 22106015 | 10/1989 | United Kingdom | A61F 2/36 |

*Primary Examiner*—Randall L. Green
*Assistant Examiner*—Dinh X. Nguyen
*Attorney, Agent, or Firm*—Michael Q. Tatlow

[57] ABSTRACT

A hip prosthesis is disclosed which employs a number of cement spacers located on the surface of the stem of the prosthesis immediately below a collar which makes direct and parallel contact with calcar bone when a stem of the prosthesis is seated in medullary canal of the patient. The collar is constructed to provide even stress distribution to the bone.

8 Claims, 4 Drawing Sheets

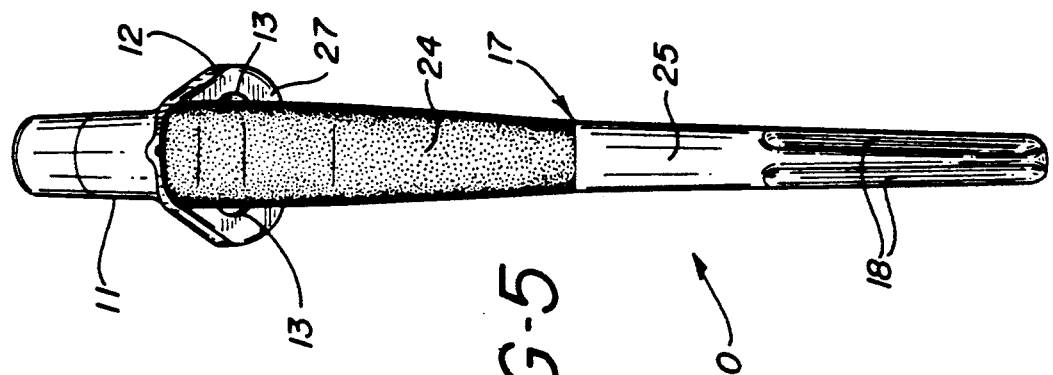
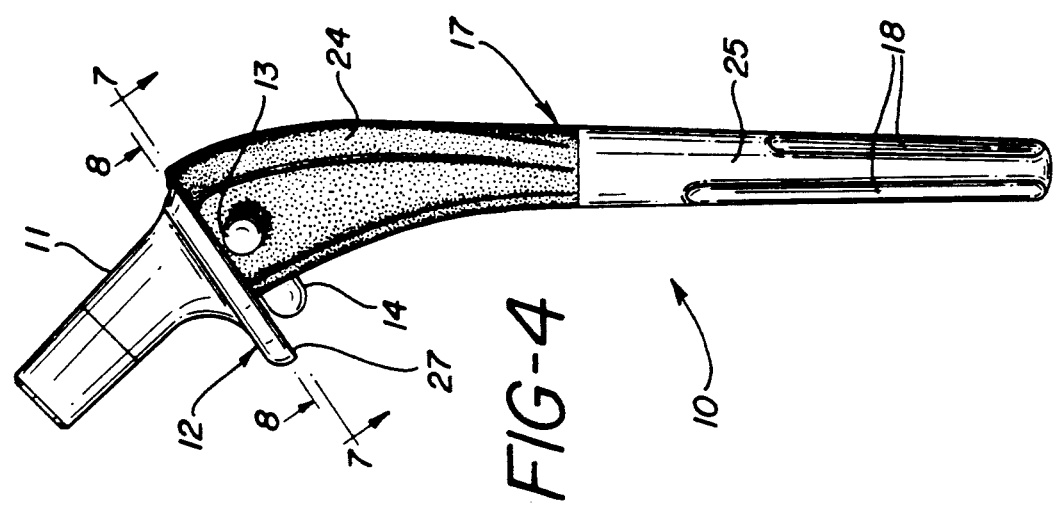
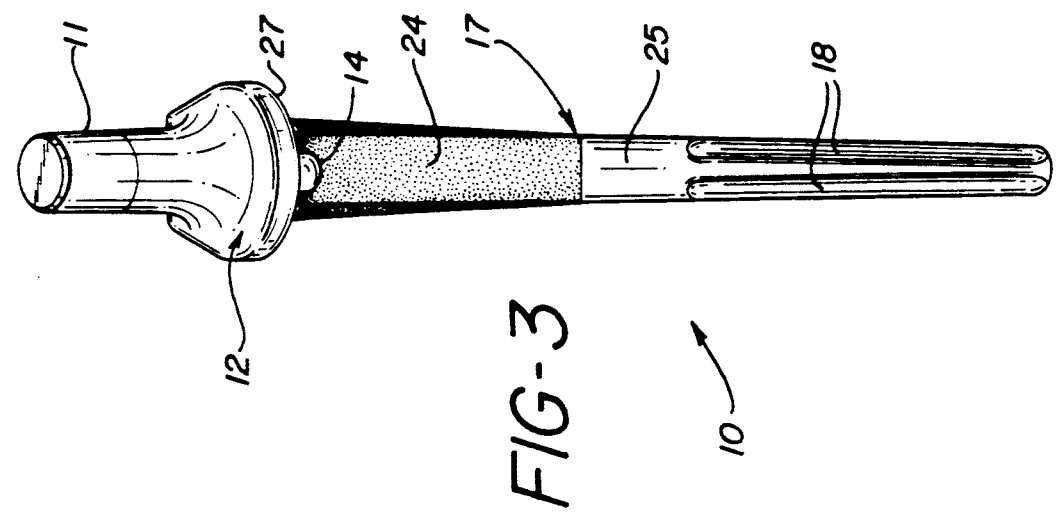

HIP PROSTHESIS

This is a continuation, of application Ser. No. 769,030, filed Sep. 30, 1991.

BACKGROUND OF THE INVENTION

1. Field of the Invention

The present invention relates to a hip prosthesis and more particularly to the femoral component of a hip prosthesis. The prosthesis of the present is the type that is cemented in position in the medullary canal of the femur. The hip of the present invention employs spacers to accurately position the prosthesis in the medullary canal to create a cement mantle of optimal thickness and to ensure neutral positioning of the prosthesis in the medullary canal. The prosthesis may also be provided with a collar that will optimally contact the calcar when implanted.

2. Prior Art

Total hip prosthesis have been in use for some time. These prosthesis generally comprise a femoral component which includes a stem or shaft, a neck and a spherical ball mounted on the neck. The ball is positioned into the second major component of the prosthesis which is an acetabular cup. The acetabular cup generally made from ultra high molecular weight polyethylene and includes a spherical opening to receive and contain the ball of the femoral component The normal movement of the leg is facilitated by the ball of the femur freely moving in the spherical cavity of the acetabular cup.

Some femoral components of hip prosthesis include a collar which is below the neck of the prosthesis and which is in contact with the bone in the femur. The particular configuration of the collar in prior art prosthesis has considerable variation.

U.S. Pat. No. 4,851,004, U.S. Pat. No. 4,068,324 and DES. 280,020 disclose hip prosthesis with a collar or flange which is somewhat elliptical in shape and has a greatest width at the lateral portion of the collar.

U.S. Pat. No. 4,642,124, U.S. Pat. No. 4,516,277, U.S. Pat. No. 4,514,865 and DES. 254,987 disclose collars which are essentially round U.S. Pat. Nos. 4,795,472 and 4,871,369 disclose hip prosthesis that have a collar that extends medially from the stem.

SUMMARY OF THE INVENTION

The prosthesis of the present invention provides cement spacers which are located on the stem of the prosthesis distal to the collar which, on implantation, locate the stem or shaft in the medullary canal in a position to provide optimal thickness of the cement mantle. This ensures that the shaft is in a neutral position verses a varus or valgus position in the medullary canal. This positioning also ensures long term stability of the bone-cement-stem interface.

The present invention also provides a femoral component for a hip prosthesis which includes a collar which is constructed so that it makes direct and parallel contact with the calcar bone when it is fully seated. The use of this collar promotes even stress distribution to the bone and to the cement mantle which is used to maintain and secure the stem of the prosthesis in the medullary canal. The stressing of the bone by the contact of the collar with the calcar reduces resorption which may occur in the absence of contact between the prosthesis and the bone.

BRIEF DESCRIPTION OF THE DRAWINGS

In the drawings.

FIG. 3 is a front view or lateral view of the prosthesis of the present invention.

FIG. 4 is a view of the anterior or posterior side of the prosthesis of the present invention.

FIG. 5 is a view of the lateral side of the prosthesis of the present invention.

DETAILED DESCRIPTION OF THE INVENTION

Figure 1:
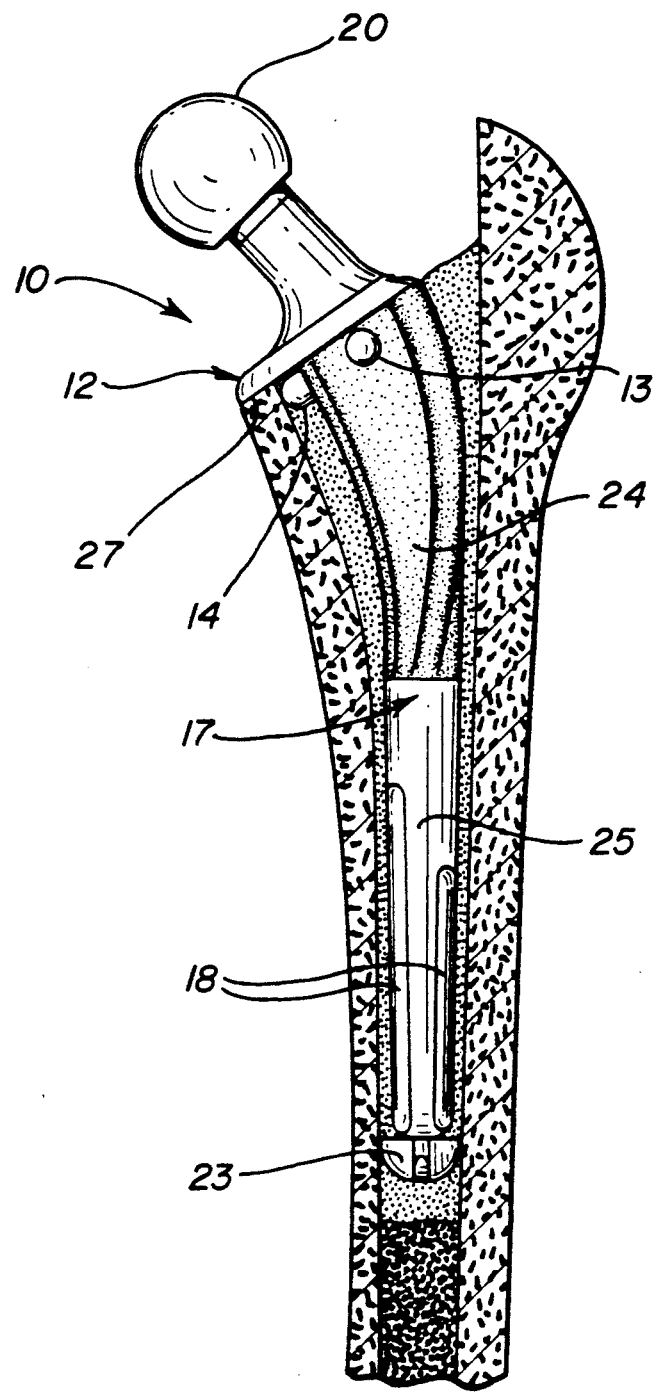
FIG. 1 is a partially cross sectional view of a femur showing the placement of the prosthesis of the present invention when implanted.
Figure 2:
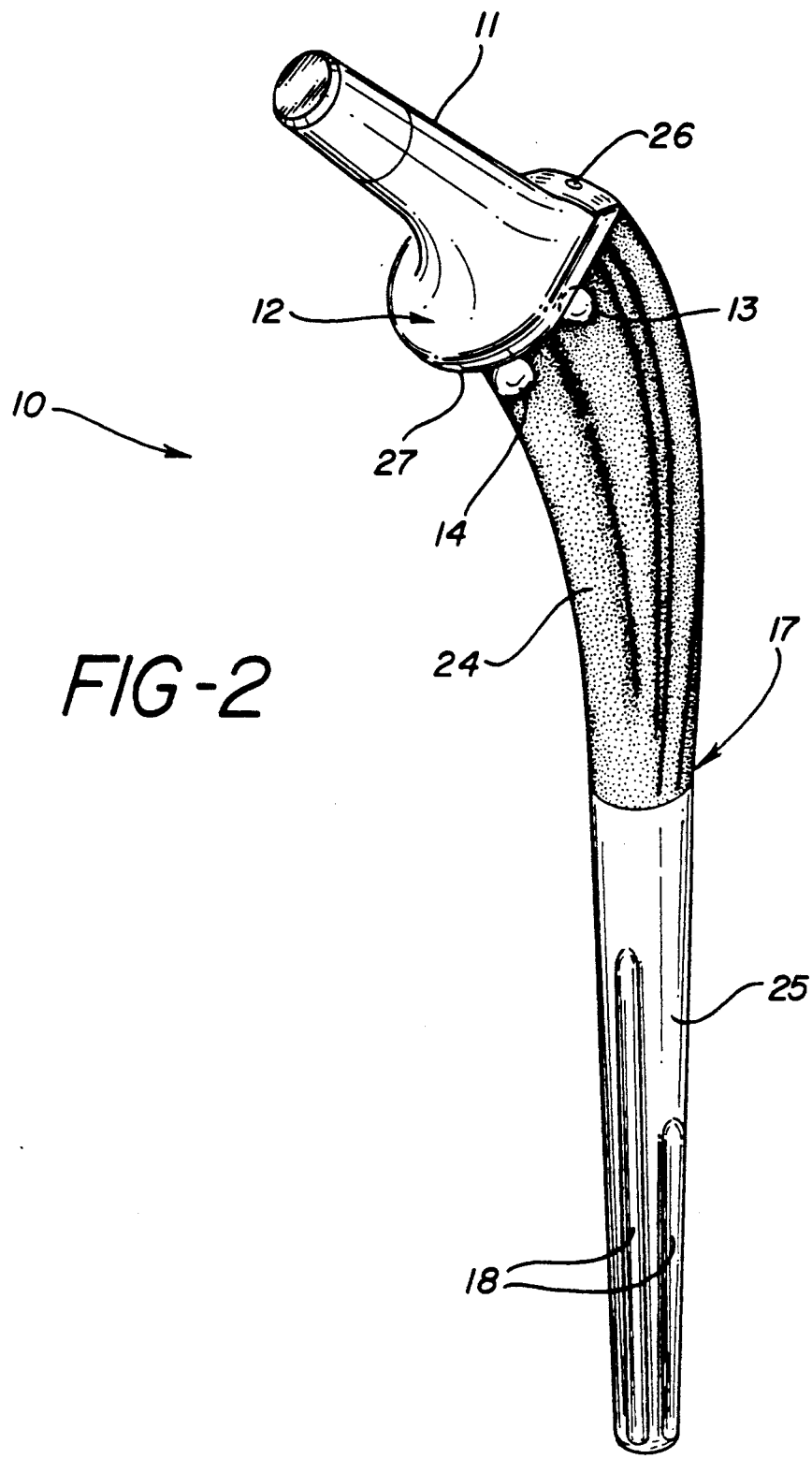
FIG. 2 is an isometric view of the femoral component of the present invention.
Figure 6:
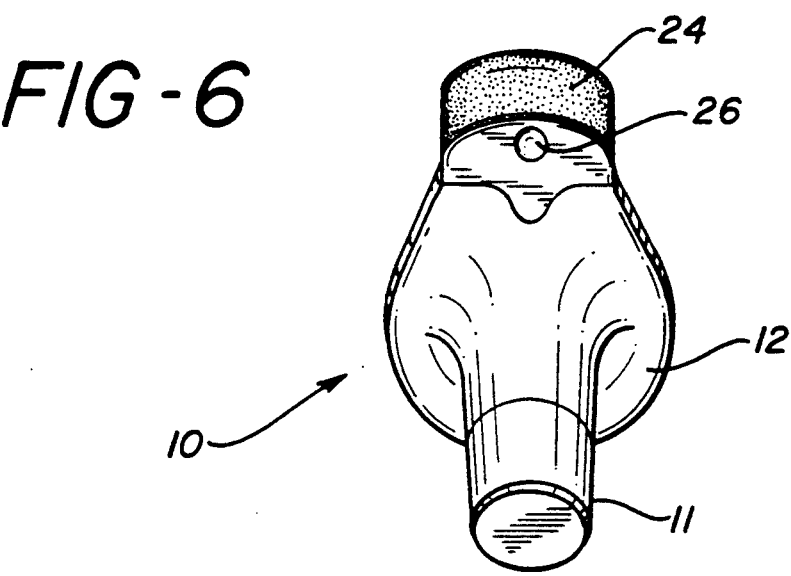
FIG. 6 is a top view of the prosthesis of the present invention.

The prosthesis of the present invention includes a shaft or stem 17 which is configured to fit into a medullary canal in a human patient The upper or proximal portion of the stem 24 can be provided with a finish to provide better adherence of a cement to this portion of the prosthesis. The lower or distal portion of the stem 25 may have a number of flutes 18 which facilitate the retention of cement in contact with the prosthesis.

The proximal end of the prosthesis has a neck 11 which has a standard, Morse type taper to allow the fixing of a spherical ball to the stem. The ball will be positioned in the acetabular cup in the total hip prosthesis. Immediately below the neck 11 is a collar 12 which is configured to have maximal contact with the bone of the patient when the stem is fully seated.

Figure 8:
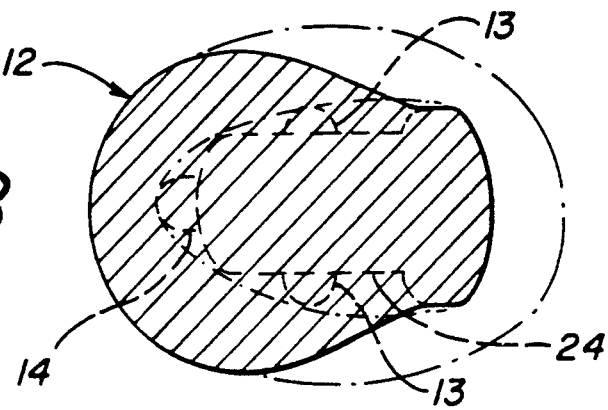
FIG. 8 is cross sectional view of the prosthesis of the present invention taken along the line 8—8 of FIG. 4.

The collar, as shown in FIGS. 3, 4, and 5, extends medially from the lateral side of the stem. The collar is larger in cross section than the stem in the anterior, posterior and medial directions. The cross section of the collar and its relationship to the cross section of the bone is depicted in FIG. 8. The collar is configured to maintain maximum contact with the calcar. This is also shown in FIG. 1.

Figure 7:
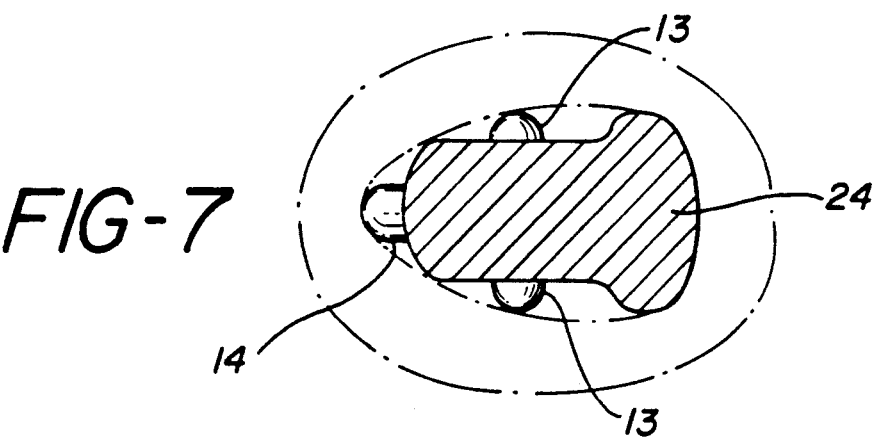
FIG. 7 is a cross sectional view of the prosthesis of the present invention taken along the line 7—7 of FIG. 4.

Immediately below collar 12 there are a number of cement spacers 13 and 14. The spacers may all be the same configuration but generally, the spacer 14 which is on the medial side of the stem is somewhat longer than the spacers 13 on the anterior and posterior sides of the stem. The spacers can be made of any material, metal or plastic, but are preferably made from polymethylmethacrylate which is the material that is generally used for the bone cements used to affix hip prosthesis in the medullary canal. The purpose of the spacers is to position the stem in what is termed a neutral position in the medullary canal of the femur. The relationship between the spacers and the bone is depicted in FIG. 7. The position is neutral the stem is not tilted medially or laterally. The spacers are preferably spherical but could be made in other configurations, such as rectangular or eliptical. The anterior and posterior spacers are generally between about 2 and 4 millimeters in length, measured from the surface of the stem to the end of the spacer. The preferred length is approximately 3.5 in millimeters. The medial spacer may be the same dimensions but it is preferable to use a medial spacer which is approximately 4 to 6 millimeters in length measured from the surface of the stem. The diameter of the spacers is approximately 6.5 millimeters in the preferred embodiment. The spacers are positioned in such a way that the proximal edge of the spacer is in close proximity to the distal edge of the collar 27. Generally, the proximal edge of the spacer is between 1 and 5 millimeters from the distal surface of the collar. More preferably, the distance between the proximal edge of the spacer and the distal edge of the collar is less than the radius of the spacer or an equivalent distance if the spacer of not circular, i.e., center line of the spacer to its proximal edge of the spacer. The spacers can be affixed to the stem by an adhesive or a hole may be drilled into the stem and the spacer fitted in the hole. The distal end of the stem 17 is positioned by the use of a distal centralizer 23, shown in FIG. 1.

There is a wing 24 at the lateral side of the stem which provides some assistance in properly compressing cement when the stem is inserted into the medullary canal. The collar 12 of the prosthesis is designed to provide maximum contact with the calcar or the solid portion of the bone. The cross sectional area of the collar is larger than the cross sectional area of the stem adjacent the collar. This is shown by a comparison between FIG. 7 and FIG. 8. This provides stress loading of the bone, particularly on the medial side of the prosthesis. Stress loading has been found to minimize bone resorption. That is, if there is no stress on the bone there is a greater tendency of the bone to resorb or disappear. This resorption of bone around an implanted prosthesis has a tendency to cause an uneven stress distribution to the bone which may result in breakage of the bone as well stress cracking and eventual failure of the cement. The configuration of the collar of the present invention provides optimum contact with the medial side of the bone as well as provides maximum contact with the cut calcar on the medial, anterior and posterior aspects. The collar has a medial periphery which is generally circular until it overlies the medial edge portion of the stem. At that point, the anterior and posterior portions of the collar extend towards the lateral edge of the prosthesis at an angle of approximately 45°. That is, an angle between the anterior or posterior edges of the collar and the center line of the collar or the center line of the stem would be approximately 22½ degrees so that the angle between the anterior and posterior edges of the collar would be 45°. This 45° angle can be varied by some amount, approximately 5 degrees, so that generally, the angle between the posterior and anterior edges of the collar would be between 40° and 50° with a 45° angle being preferred. This configuration provides optimum contact of the collar with calcar.

There is a impact hole 26 at the lateral edge of the prosthesis. The purpose of this impact hole is to allow the insertion and fixing of a tool which might be used to provide a position along the center line of the stem to apply force to position the stem in the medullary canal.

We claim:

1. A femoral component of a hip prosthesis comprising a neck adapted to receive a ball head, a collar having a proximal surface on the side of the neck and a distal surface on the side of a stem, said stem being capable of insertion into the medullary canal of the femur of a patient, said collar having a cross sectional area larger than the cross sectional area of part of the stem adjacent the collar, said stem having anterior, posterior, medial and lateral surfaces, and said collar having anterior, posterior and medial edges that extend beyond the anterior, posterior and medial surfaces of the stem, a cement spacer located on each of the anterior, posterior and medial surfaces of the stem, each of said spacers having a generally circular cross section and having a proximal edge and a center line through the center of said spacer, each of said spacers extending outwardly from the stem surface on which it is located, said spacers being affixed to the stem immediately adjacent the distal surface of the collar whereby the spacers may position the stem when the stem is placed in the medullary canal of the femur of a patient.

2. The prosthesis of claim 1 in which the spacers are made of polymethylmethacrylate.

3. The prosthesis of claim 1 in which the spacers have a generally spherical shape.

4. The prosthesis of claim 1 in which the medial spacer is longer than the anterior and posterior spacers.

5. The prosthesis of claim 1 in which the spacers are affixed to the stem so that the center line of the spacers are positioned a distance from the distal surface of the collar which is less than the distance between the center line of the spacer and its proximal edge.

6. The prosthesis of claim 1 in which the proximal edge of the spacer is between 1 and 5 millimeters from the distal surface of the collar.

7. The prosthesis of claim 1 having an angle formed between the anterior and posterior edges of the collar that is between 40° and 50°.

8. The prosthesis of claim 7 in which the collar terminates medially from the lateral surface of the stem.

* * * * *